United States Patent
Geng et al.

(10) Patent No.: US 10,941,116 B2
(45) Date of Patent: Mar. 9, 2021

(54) CRYSTALLINE FORMS OF MESACONINE AND PREPARATION METHODS THEREFOR

(71) Applicant: Gooddoctor Pharmaceutical Group Co., Ltd., Sichuan (CN)

(72) Inventors: Yuefei Geng, Sichuan (CN); Funeng Geng, Sichuan (CN); Xiuying Ma, Sichuan (CN); Ruobing Chao, Sichuan (CN)

(73) Assignee: Gooddoctor Pharmaceutical Group Co., Ltd. (CN)

( * ) Notice: Subject to any disclaimer, the term of this patent is extended or adjusted under 35 U.S.C. 154(b) by 0 days.

(21) Appl. No.: 16/963,026

(22) PCT Filed: Jan. 23, 2019

(86) PCT No.: PCT/CN2019/072874
§ 371 (c)(1),
(2) Date: Jul. 17, 2020

(87) PCT Pub. No.: WO2019/144889
PCT Pub. Date: Aug. 1, 2019

(65) Prior Publication Data
US 2020/0339514 A1 Oct. 29, 2020

(30) Foreign Application Priority Data

Jan. 24, 2018 (CN) .......................... 201810071927.2

(51) Int. Cl.
*C07D 221/22* (2006.01)
(52) U.S. Cl.
CPC ........ *C07D 221/22* (2013.01); *C07B 2200/13* (2013.01)
(58) Field of Classification Search
None
See application file for complete search history.

(56) References Cited

FOREIGN PATENT DOCUMENTS

| CN | 101759640 A | 6/2010 |
|---|---|---|
| CN | 102146057 A | 8/2011 |
| CN | 102146057 B | 11/2012 |
| CN | 102977020 A | 3/2013 |

OTHER PUBLICATIONS

Aconitum carmichaeli Debx., vol. 1, the Chinese Pharmacopoeia, 2015 edition, pp. 191-193.
Determination method of the melting point, the first method of 0612, general rule, vol. 4, The Chinese Pharmacopoeia, 2015 Edition, pp. 75-76.
Guiding principle for stability test of raw materials of drugs and preparations, general rule 9001, the Chinese Pharmacopoeia, 2015 edition, pp. 354-356.
International Search Report for Application No. PCT/CN2019/072874, dated Apr. 15, 2019, pp. 1-2.
Jian, et al, Structure-Cardiac Activity Relationship of C19-Diterpenoid Alkaloids, Natural Product Communications, accepted Apr. 2012, pp. 713-720, vol. 7, No. 6.
Liu, et al., Cardioactive C19-Diterpenoid Alkaloids from the Lateral Roots of Aconitum carmichaeli "Fu Zi", Chem. Pharm. Bull., published online Oct. 2011, pp. 144-149, vol. 60, No. 1.
Morio S.I., Aconitum Alkaloids. VI. Mesaconitine, a Second New Aconitum Alkaloid, Justus Liebigs Annalen der Chemie, Dec. 1929, pp. 189-190, ISSN: 0075-4617. (Abstract only).
Sakai, S. et al, Partial Synthesis of Isodelphinine and Penduline, Yakugaku Zasshi, received Jan. 1984, pp. 747-748, vol. 104, No. 7, ISSN: 0031-6903. (English abstract provided).
The definition of hygroscopicity in Chinese Pharmacopoeia, general rule 9103, vol. 4, 2015 Edition, pp. 378-379.
The method of solubility test in the Chinese Pharmacopoeia, 2015 edition, general notice, pp. 378-379.
Zhang, et al., Further Studies on Structure-Cardiac Activity Relationships of Diterpenoid Alkaloids, Natural Product Communications, accepted Aug. 2015, pp. 2075-2084, vol. 10, No. 12.
Caira, Crystalline Polymorphism of Organic Compounds, Topics in Current Chemistry, 1998, pp. 163-208, vol. 198.

*Primary Examiner* — Brian J Davis
(74) *Attorney, Agent, or Firm* — Lerner, David, Littenberg, Krumholz & Mentlik, LLP (57) ABSTRACT

The present invention relates to crystalline forms of mesaconine. Specifically, the present invention relates to crystalline form A, crystalline form B and crystalline form C of mesaconine and preparation methods thereof. In the method, the mesaconine is crystallized in solvent, and then the crude crystal is dried to obtain target crystalline form. The crystalline forms of mesaconine according to the present invention have good solubility, good stability, low hygroscopicity, long-term storage capability and good reproducibility, and have a good prospect to be developed as pharmaceuticals.

6 Claims, 6 Drawing Sheets

CRYSTALLINE FORMS OF MESACONINE AND PREPARATION METHODS THEREFOR

CROSS-REFERENCE TO RELATED APPLICATIONS

The present application is a national phase entry under 35 U.S.C § 371 of International Application No. PCT/CN2019/072874 filed Jan. 23, 2019, which claims priority from Chinese Application No. 201810071927.2 filed Jan. 24, 2018, all of which are hereby incorporated herein by reference.

TECHNICAL FIELD

The present invention relates to the field of crystalline forms, in particular to crystalline forms of mesaconine and preparation methods therefor.

BACKGROUND

The traditional Chinese medicine monkshood is a processed product obtained from rootlet of *Aconitum carmichaeli* Debx., which has the effects of rescuing from collapse by restoring yang, eliminating wind-cold-dampness, warming the meridian to relieve pain (volume 1, *Chinese pharmacopoeia*, 2015 edition). And it is widely used in the clinic as a famous traditional Chinese medicine.

Studies have found that mesaconine is the main cardiotonic active ingredient of monkshood, as recorded in the following documents: Xiu-Xiu Liu, et al, *Chem. Pharm. Bull*, 2012, 60(1), 144-149; Xi-Xian Jian, et al, *Nat. Prod. Commun*, 2012, 7(6), 713-720; Chinese invention patent, 2012, CN102146057B; Zhong-Tang Zhang, et al, *Nat. Prod. Commun*, 2015, 10(12), 2075-2084. Therefore, mesaconine has a prospect of developing into anti-heart failure drugs and drugs for treating other diseases.

Mesaconine has a chemical name of N-methyl-1α,6α,16β,18-tetramethoxyl-4-methyl-aconite-3α,8β,13β,14α,15α-pentol with a molecular formula of $C_{24}H_{39}NO_9$ and a CAS No: 6792-09-2, and has a structure represented by the following Structural Formula.

Chinese invention patent CN 102146057 B discloses a method for preparing mesaconine, and the mesaconine obtained thereby is amorphous powder. However, the amorphous powder easily absorbs moisture and is not suitable for long-term storage.

At present, there is no report on crystalline form of mesaconine, so it is necessary to research and develop crystalline form of mesaconine with improved physical and chemical properties and bioavailability and the like.

SUMMARY OF THE INVENTION

An object of the present invention is to provide crystalline forms of mesaconine which have improved solubility, stability, hygroscopicity and processibility (filtration, drying, etc.).

In a first aspect of the present invention, it provides a crystalline form of mesaconine, hereinafter referred to as crystalline form A of mesaconine, which exhibits characteristic peaks at 2θ of 8.3°±0.2°, 10.6°±0.2°, 13.3°±0.2°, 13.7°±0.2° and 19.0°±0.2° in powder X-ray diffraction spectrum using Cu-Kα radiation.

Further, the crystalline form A of mesaconine according to the present invention also exhibits characteristic peaks at 2θ of 11.6°±0.2°, 19.8°±0.2°, 24.2°±0.2° and 26.9°±0.2° in powder X-ray diffraction spectrum using Cu-Kα radiation.

Figure 1:
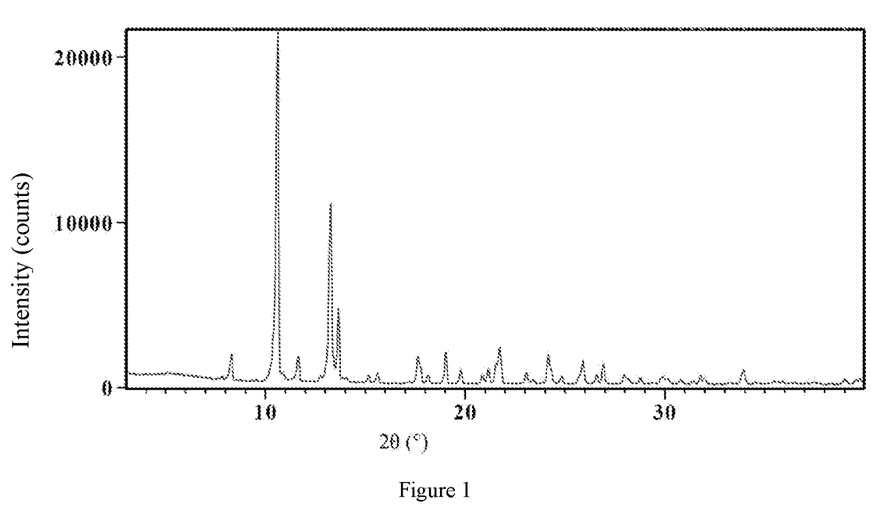
FIG. 1 is an XRPD spectrum of the crystalline form A of mesaconine.

Without limitation, the crystalline form A of mesaconine according to the present invention exhibits a powder X-ray diffraction (XRPD) spectrum as shown in FIG. 1.

Figure 2:
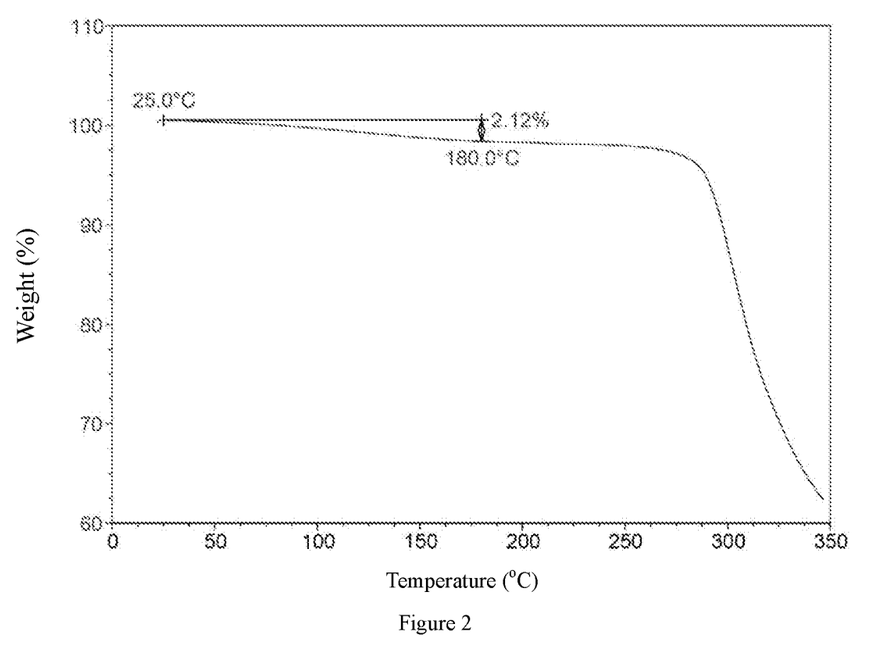
FIG. 2 is a TGA spectrum of the crystalline form A of mesaconine.

Without limitation, the crystalline form A of mesaconine according to the present invention exhibits a thermogravimetric analysis (TGA) spectrum as shown in FIG. 2.

Figure 3:
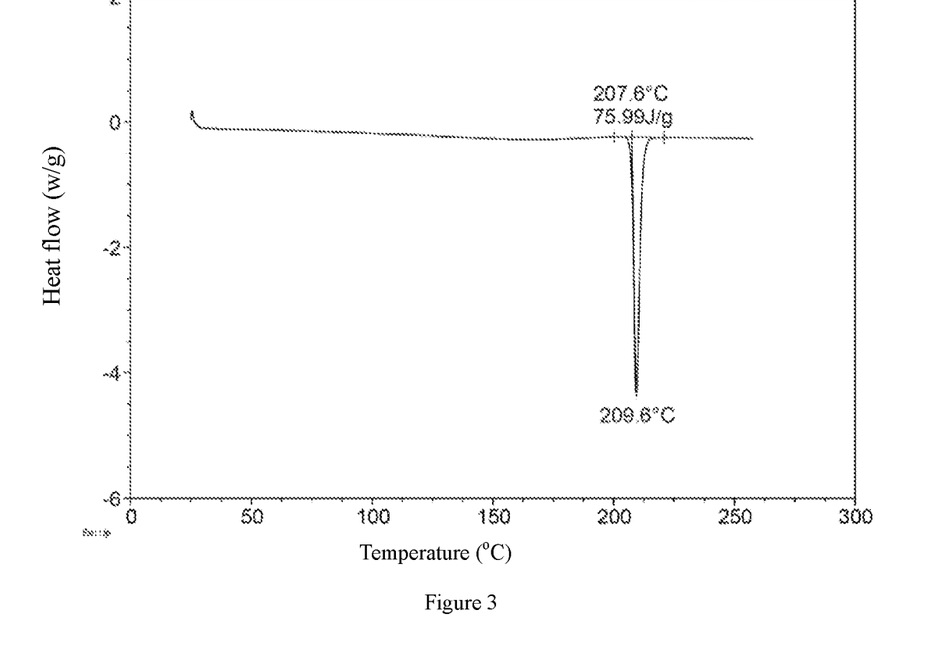
FIG. 3 is a DSC spectrum of the crystalline form A of mesaconine.

Without limitation, the crystalline form A of mesaconine according to the present invention exhibits a differential scanning calorimetry (DSC) spectrum as shown in FIG. 3.

The present invention also provides a method for preparing the crystalline form A of mesaconine comprising the steps:

(1) adding mesaconine into a solvent, then heating the obtained solution to 50~90° C. (preferably, 60~80° C.) to dissolve the mesaconine so as to obtain a mesaconine solution;

(2) cooling the mesaconine solution to −10~30° C. (preferably 0~30° C., more preferably 20~30° C.), stirring the solution to precipitate crystal, and then performing filtration; (3) drying the solid obtained by filtration in the step (2) at vacuum to obtain the crystalline form A of mesaconine.

In the method for preparing the crystalline form A of mesaconine according to the present invention, the solvent is one or more selected from a group consisting of water, methanol, ethanol, isopropanol, acetone and acetonitrile.

In a second aspect of the present invention, it provides another crystalline form of mesaconine, hereinafter referred to as crystalline form B of mesaconine, which exhibits characteristic peaks at 2θ of 6.6°±0.2°, 9.2°±0.2°, 13.4°±0.2°, 14.3°±0.2° and 15.5°±0.2° in powder X-ray diffraction spectrum using Cu-Kα radiation.

Further, the crystalline form B of mesaconine according to the present invention also exhibits characteristic peaks at 2θ of 18.3°±0.2°, 20.2°±0.2°, 23.6°±0.2° and 24.2°±0.2° in powder X-ray diffraction spectrum using Cu-Kα radiation.

Figure 6:
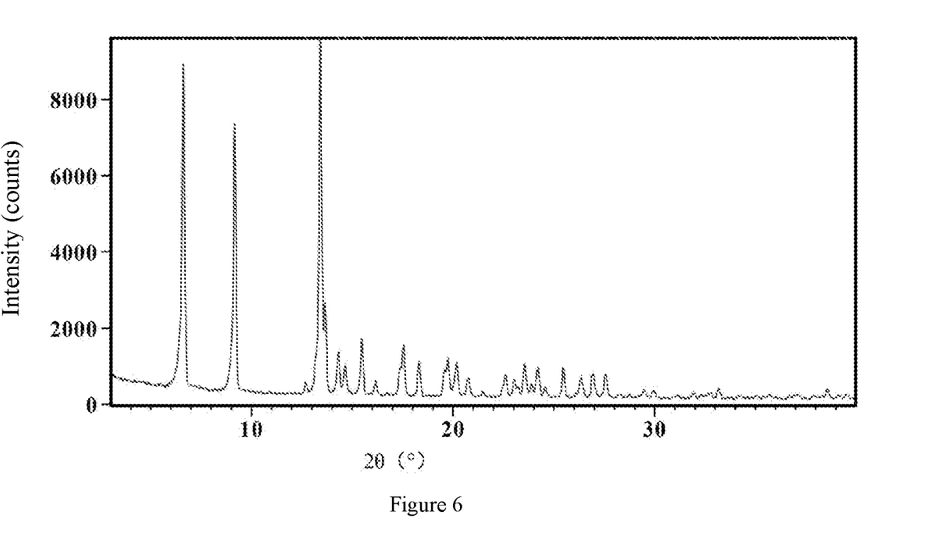
FIG. 6 is an XRPD spectrum of the crystalline form B of mesaconine.

Without limitation, the crystalline form B of mesaconine according to the present invention exhibits a XRPD spectrum as shown in FIG. 6.

Figure 7:
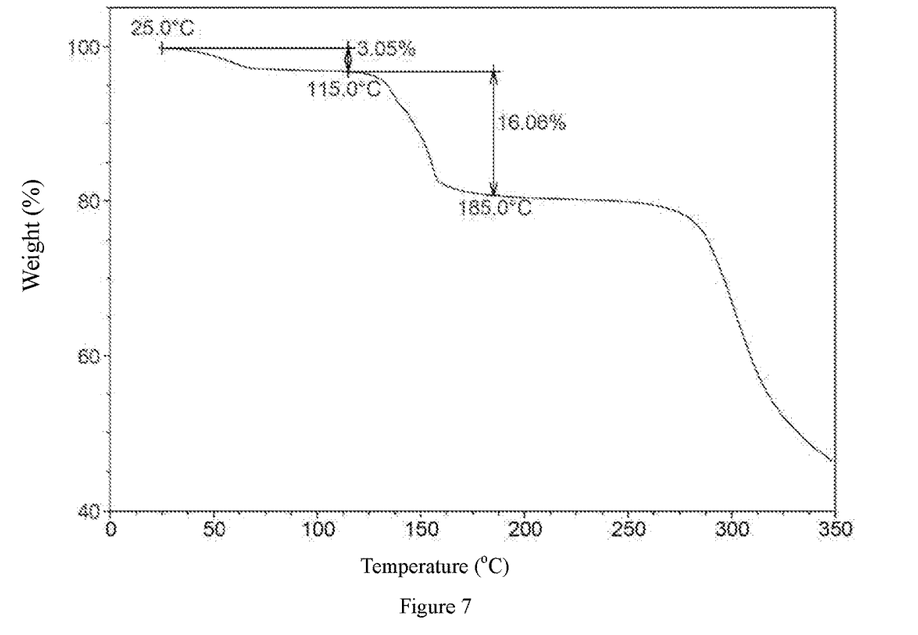
FIG. 7 is a TGA spectrum of the crystalline form B of mesaconine.

Without limitation, the crystalline form B of mesaconine according to the present invention exhibits a TGA spectrum as shown in FIG. 7.

Figure 8:
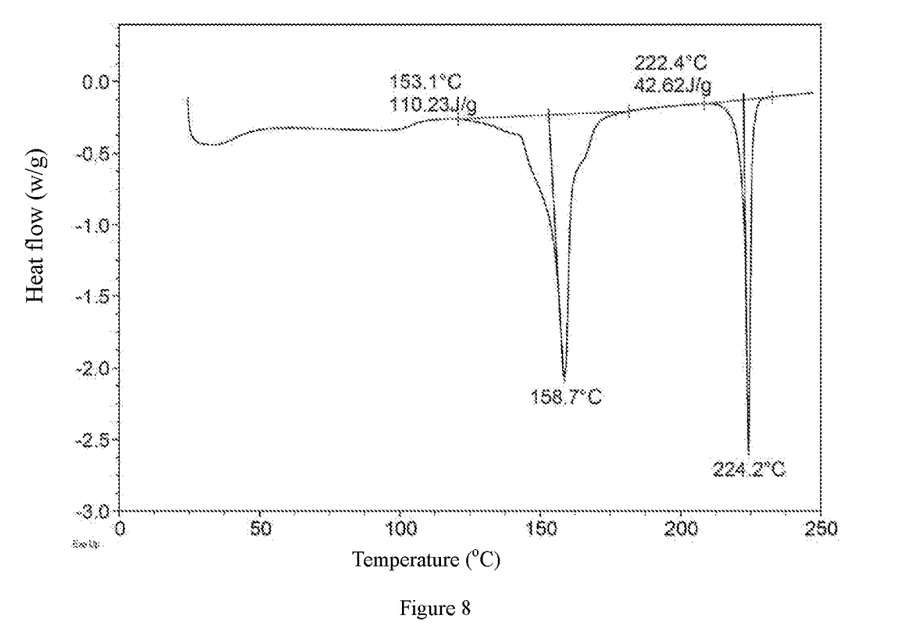
FIG. 8 is a DSC spectrum of the crystalline form B of mesaconine.

Without limitation, the crystalline form B of mesaconine according to the present invention exhibits a DSC spectrum as shown in FIG. 8.

The invention also provides a method for preparing the crystalline form B of mesaconine comprising steps:

(1) suspending and stirring the crystalline form A of mesaconine in an organic solvent at 40~60° C. to obtain a suspension;

(2) cooling the suspension to −10~30° C. (preferably 0~30° C., more preferably 20~30° C.), stirring the suspension to precipitate crystal, and then performing filtration;

(3) drying the solid obtained by filtration in the step (2) at vacuum to obtain crystalline form B of mesaconine.

In the method for preparing the crystalline form B of mesaconine according to the present invention, the organic solvent is N-methylpyrrolidone.

In a third aspect of the present invention, it provides another crystalline form of mesaconine, hereinafter referred to as crystalline form C of mesaconine, which exhibits characteristic peaks at 2θ of 7.90°±0.2°, 10.1°±0.2°, 13.0°±0.2°, 17.4°±0.2° and 19.4°±0.2° in powder X-ray diffraction spectrum using Cu-Kα radiation.

Further, the crystalline form C of mesaconine according to the present invention also exhibits characteristic peaks at 2θ of 19.9°±0.2°, 21.0°±0.2°, 23.8°±0.2° and 26.6°±0.2° in powder X-ray diffraction spectrum using Cu-Kα radiation.

Figure 10:
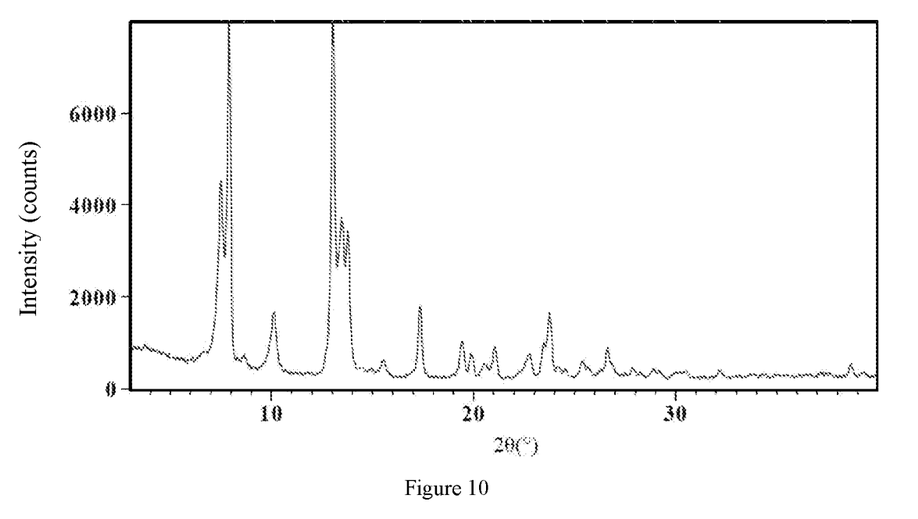
FIG. 10 is an XRPD spectrum of the crystalline form C of mesaconine.

Without limitation, the crystalline form C of mesaconine according to the present invention exhibits a XRPD spectrum as shown in FIG. 10.

Figure 11:
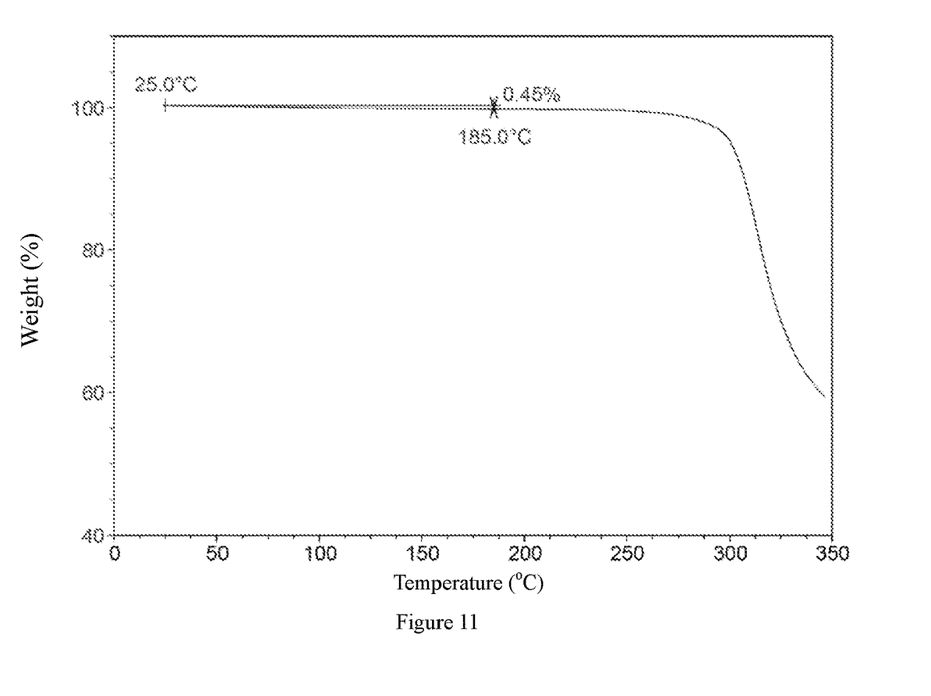
FIG. 11 is a TGA spectrum of the crystalline form C of mesaconine.

Without limitation, the crystalline form C of mesaconine according to the present invention exhibits a TGA spectrum as shown in FIG. 11.

Figure 12:
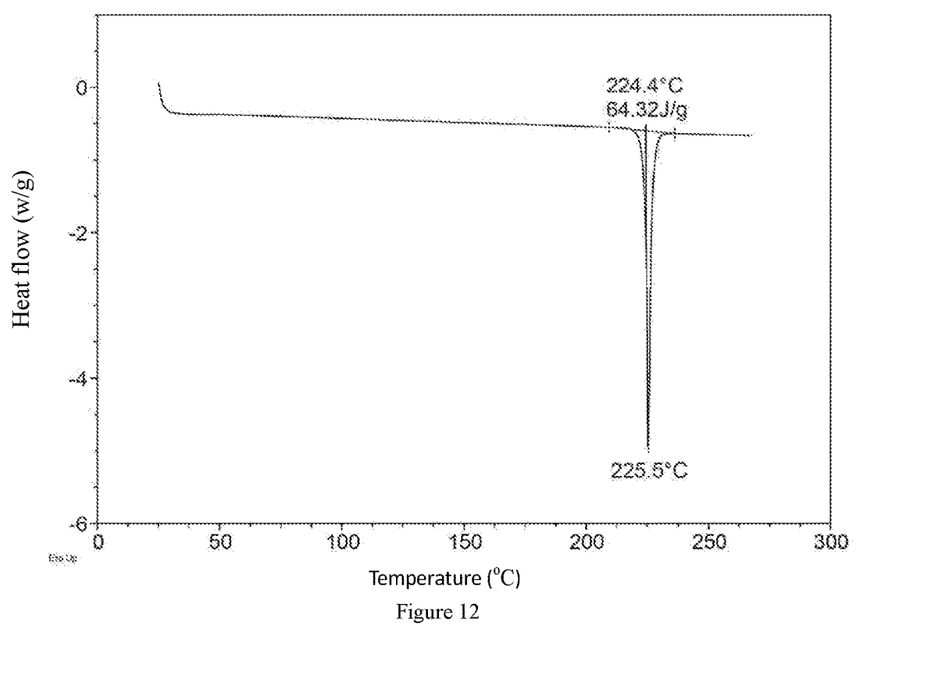
FIG. 12 is a DSC spectrum of the crystalline form C of mesaconine.

Without limitation, the crystalline form C of mesaconine according to the present invention exhibits a DSC spectrum as shown in FIG. 12.

The invention also provides a method for preparing the crystalline form C of mesaconine comprising steps of:
heating the crystalline form B of mesaconine at vacuum to obtain crystalline form C of mesaconine.

In the method for preparing crystalline form C of mesaconine according to the present invention, the heating temperature is 140~230° C., preferably 170~200° C.

In a fourth aspect of the present invention, it provides a pharmaceutical composition comprising the crystalline form A of mesaconine, the crystalline form B of mesaconine or the crystalline form C of mesaconine of the present invention, and pharmaceutically acceptable excipients.

In a fifth aspect of the present invention, it provides a use of the crystalline form A of mesaconine, the crystalline form B of mesaconine or the crystalline form C of mesaconine, or a pharmaceutical composition thereof in preparation of cardiotonic and anti-heart failure drugs.

The crystalline forms of mesaconine prepared by the present invention are superior to amorphous mesaconine in stability, hygroscopicity and processibility.

MODE OF CARRYING OUT THE INVENTION

The following examples further illustrate the present invention, however, the scope of the present invention is not limited thereto.

Mesaconine used in the following examples was prepared according to the following method.

I. Extraction of Total Alkaloid from *Aconitum* Plants of *Aconitum soongaricum* Stapf (1) 10 kg of dried root of *Aconitum* Plants of *Aconitum soongaricum* Stapf was pulverized, and then was sieved with 20 mesh sieve to obtain powder;

(2) the powder of the *Aconitum* Plants of *Aconitum soongaricum* Stapf was successively extracted with 80 L, 36 L and 24 L of aqueous solution comprising 5% sulfuric acid and 85% ethanol under reflux for 3 times and 2 hours for each extraction, and then the mixture was filtering, and filtrate was combined;

(3) the filtrate was concentrated under reduced pressure to recover ethanol until the relative density of the fluid extract was 1.05~1.10, and then 0.46 kg of the fluid extract was collected;

(4) the fluid extract was diluted with 1.4 L of water, alkalized with ammonia water, adjusted to pH=10, and then extracted in an extractor with ethyl acetate (2L×3 times) and stirred for 5~10 min each time, and extract was collected;

(5) the obtained extract was concentrated under reduced pressure to recover ethyl acetate and obtain 129 g of total alkaloid. The total alkaloid was sampled and the content in percentage of aconitine in the total alkaloid was determined by HPLC method. The total content of the aconitine (I) in the total alkaloid was 42.5 g with a yield of 0.42% through calculation based on the content in percentage as determined above and wet weight of the total alkaloid.

II. Preparation of Mesaconine

(1) Preparation of Aconine (II)

After 100 g of total alkaloid (including 33 g of aconitine) was dissolved in 500 ml of 95% ethanol, 7.2 g (78 mmol) of sodium hydroxide was added thereto, and stirred at room temperature for 2 hours, and the solvent was recovered under reduced pressure to obtain 120 g of solid. The solid was diluted with 1000 ml of water and extracted with dichloromethane (500 ml×2 times). The aqueous layer was adjusted to pH=5 with concentrated hydrochloric acid, then adjusted to pH=11~12 with diluted solution of sodium hydroxide in ethanol. The obtained mixture was concentrated to dryness under reduced pressure to obtain 90 g of solid. 900 ml of dichloromethane-anhydrous ethanol (9:1, V/V) was added to the solid to dissolve it under heating. Thus obtained mixture was filtered and the filtrate was concentrated under reduced pressure to obtain solid. Thus obtained solid was crystallized in hot boiled isopropanol-water (100:5) to obtain 22.5 g of the target compound.
Yield: 86%, white amorphous powder, $C_{25}H_{41}NO_9$.

(2) Preparation of 3,14,15-triacetyl aconine(III)

10.0 g(20 mmol) of aconine (II) was mixed with 7.1 g(70 mmol) of acetic anhydride and 100 ml of pyridine, and the mixture was reacted under reflux for 2.5 hours. After reaction, thus obtained mixture was concentrated under reduced pressure to obtain a residue. The residue was diluted with 170 ml of water, alkalized with ammonia water to pH=9~10, then thus obtained mixture was extracted with dichloromethane (80 ml×3). The extract was combined, dried over anhydrous sodium sulfate, and concentrated under reduced pressure to obtain a solid. Thus obtained solid was subjected to silica-gel column chromatography using dichloromethane-anhydrous ethanol (200:1) as eluent to obtain 10.7 g of the target compound.
Yield: 85.6%, white amorphous powder, $C_{31}H_{47}NO_{12}$.

(3) Preparation of N-desethyl-3,14,15-triacetyl aconine (V)

10.0 g (17 mmol) of 3,14,15-triacetyl aconine (III) was dissolved in 100 ml of glacial acetic acid, 9.9 g (66 mmol) of N-bromosuccinimide was added thereto, and the mixture was stirred at room temperature for 2 hours. Then the obtained mixture was concentrated under reduced pressure to obtain a solid. The solid was dissolved in a small amount of dichloromethane, 150 ml of water was added thereto. Thus obtained mixture was alkalized with concentrated ammonia water to pH=10, and then extracted with dichloromethane (80 ml×2). The extract was combined, dried over anhydrous sodium sulfate, concentrated under reduced pressure to obtain 10.5 g of solid. Thus obtained solid was subjected to silica-gel column chromatography using petroleum ether-acetone (2:1) as eluent to obtain 6.4 g of the target compound.
Yield: 67.0%, white amorphous powder, $C_{29}H_{43}NO_{12}$.

(4) Preparation of 3,14,15-triacetyl mesaconine(VII)

10 g (17 mmol) of N-desethyl-3,14,15-triacetyl aconine (V) was dissolved in 25 ml of tetrahydrofuran, then 2 ml of 40% formaldehyde aqueous solution and 1 ml of glacial acetic acid were added thereto at room temperature, and the temperature was maintained while stirred for 30 minutes. Then 7.1 g (33.5 mmol) of $NaBH(OAc)_3$ was added thereto and thus obtained mixture was stirred for 30 minutes. The mixture was adjusted to pH=9 by using concentrated ammonia water, and 15 ml of water was added thereto for dilution. Thus obtained mixture was extracted twice with 20 ml of dichloromethane, the extract was combined, sequentially washed with water, dried over anhydrous sodium sulfate, and concentrated under reduced pressure to dryness to obtain 5.5 g of solid. The solid was subjected to silica-gel column chromatography using chloroform-methanol (9:1) as eluent to obtain 5.41 g of the target compound.
Yield: 53.1%, white amorphous powder, $C_{30}H_{45}NO_{12}$.

(5) Preparation of mesaconine(IX)

10 g (16.3 mmol) of 3,14,15-triacetyl mesaconine(VII) was dissolved in 75 ml of 95% ethanol solution, 2.29 g (57.2 mmol) of sodium hydroxide was added thereto and the mixture was reacted under reflux for 30 min. The reaction solution was cooled to room temperature, adjusted to pH=5 using concentrated hydrochloric acid, and then adjusted to pH=11~12 using diluted solution of sodium hydroxide in ethanol. Insoluble substance was filtered, and the filtrate was concentrated under reduced pressure to obtain solid. The solid was dissolved in 110 ml dichloromethane-absolute ethanol (9:1, V/V), thus obtained solution was suction filtered and the filtrate was concentrated to dryness under reduced pressure to obtain 7.22 g of mesaconine with a yield of 91.1%.

$^1$H NMR (400 MHz, CD$_3$OD) δ: 4.47(1H, d, J=6.0 Hz, H-15β), 4.24(1H, d, J=6.8 Hz, H-6β), 3.94, 3.51(2H, 2 xABq, J=8.4 Hz, H$_2$-18), 3.85(1H, d, J=5.2 Hz, H-14β), 3.71(1H, dd, J=11.2, 5.2 Hz, H-3β), 3.64(3H, s, OCH$_3$-16), 3.40(3H, s, OCH$_3$-6), 3.35(3H, s, OCH$_3$-18), 3.31(3H, s, OCH$_3$-1), 3.15(1H, dd, J=11.2, 6.8 Hz, H-1β), 3.08(1H, d, J=6.0 Hz, H-16), 2.96(1H, s, H-17), 2.71, 1.97(2H, 2 xABq, J=8.8 Hz, H$_2$-12), 2.65, 2.42(2H, 2 xABq, J=11.2 Hz, H$_2$-19), 2.38(1H, s, H-7), 2.35(3H, s, CH$_3$N-21), 2.31, 2.24(2H, m, H$_2$-2), 2.27(1H, m, H-9β), 2.11(1H, d, J=6.8 Hz, H-5β), 1.98(1H, m, H-10β).

Example 1

Preparation of Crystalline Form A of Mesaconine 40 ml of isopropanol was added to 10 g of mesaconine, and the mixture was heated in water bath under reflux to dissolve the mesaconine. 2 ml of water was added thereto, the mesaconine was crystallized under stirring. Thus obtained mixture was naturally cooled overnight, and then suction filtered. The filter cake was washed with a small amount of isopropanol and then the mixture was drained to collect crystal. The crystal was dried at vacuum at 85° C. for 8 hours to obtain white solid crystal. After testing, the white solid crystal was confirmed to be crystalline form A of mesaconine, and its XRPD spectrum was shown in FIG. 1. Yield: 70%, HPLC: 99.7%.

Example 2

Preparation of Crystalline Form A of Mesaconine 40 ml of isopropanol was added to 10 g of mesaconine, and the mixture was heated in water bath under reflux to dissolve the mesaconine. The mesaconine was crystallized under stirring, thus obtained mixture was naturally cooled overnight, and then suction filtered. The filter cake was washed with a small amount of isopropanol and then the mixture was drained to collect crystal. The crystal was dried at vacuum at 85° C. for 8 hours to obtain target product, i.e., crystalline form A of mesaconine. Its XRPD spectrum was consistent with that in FIG. 1. Yield: 78%, HPLC: 99.6%.

Example 3

Preparation of Crystalline Form A of Mesaconine 30 ml of ethanol was added to 10 g of mesaconine, and the mixture was heated in water bath under reflux to dissolve the mesaconine. The mesaconine was crystallized under stirring, thus obtained mixture was naturally cooled overnight, and then suction filtered. The filter cake was washed with a small amount of ethanol and then the mixture was drained to collect crystal. The crystal was dried at vacuum at 85° C. for 8 hours to obtain target product, i.e., crystalline form A of mesaconine. Its XRPD spectrum was consistent with that in FIG. 1. Yield: 58%, HPLC: 99.8%.

Example 4

Preparation of Crystalline Form A of Mesaconine 30 ml of methanol was added to 10 g of mesaconine, and the mixture was heated in water bath under reflux to dissolve the mesaconine. The mesaconine was crystallized under stirring, thus obtained mixture was naturally cooled overnight, and then suction filtered. The filter cake was washed with a small amount of methanol and then the mixture was drained to collect crystal. The crystal was dried at vacuum at 85° C. for 8 hours to obtain target product, i.e., crystalline form A of mesaconine. Its XRPD spectrum was consistent with that in FIG. 1. Yield: 38%, HPLC: 99.8%.

Example 5

Preparation of Crystalline Form A of Mesaconine 30 ml of isopropanol was added to 10 g of mesaconine, and the mixture was heated in water bath under reflux to dissolve the mesaconine. 10 ml of ethanol was added thereto, the mesaconine was crystallized under stirring, thus obtained mixture was naturally cooled overnight, and then suction filtered. The filter cake was washed with a small amount of isopropanol and then the mixture was drained to collect crystal. The crystal was dried at vacuum at 85° C. for 8 hours to obtain target product, i.e., crystalline form A of mesaconine. Its XRPD spectrum was consistent with that in FIG. 1. Yield: 68%, HPLC: 99.8%.

Example 6

Characterization of Crystalline Form A of Mesaconine

Crystalline form A of mesaconine prepared according to the method in Example 1 was sampled and subjected to the following tests.

1. X-Ray Powder Diffraction Method

Crystalline form A of mesaconine was sampled and subjected to a test on PANalytical Empyrean and X'Pert3 X-ray powder diffraction analyzer under condition: Cu, Kα, Kα1 (Å): 1.540598; Kα2 (Å): 1.544426, Kα2/Kα1 intensity ratio: 0.50, scanning range: 3~°40°. The X-ray diffraction spectrum of the crystalline form A of mesaconine sample was shown in FIG. 1, and the basic information of the XRPD spectrum of the crystalline form A of mesaconine sample was shown in Table 1.

TABLE 1

| diffraction angle (2θ, °) | interplanar spacing (d, Å) | relative intensity (%) |
|---|---|---|
| 8.29 | 10.66 | 7.39 |
| 10.61 | 8.34 | 100.00 |
| 11.64 | 7.60 | 7.38 |
| 13.26 | 6.68 | 51.22 |
| 13.65 | 6.49 | 21.16 |
| 19.03 | 4.66 | 9.06 |
| 19.78 | 4.49 | 4.07 |
| 24.15 | 3.68 | 8.13 |
| 26.91 | 3.31 | 5.52 |

It should be understood by those skilled in the art that these diffraction peaks do not represent all the details of the diffraction peaks of the crystalline form A of mesaconine. The 2θ value of XRPD can change within the error range according to the testing equipments as well as the change during preparation and the change of batches, and the quoted value should not be regarded as absolute value. In addition, the relative intensity of the peaks may vary with the orientation effect, so the intensity shown in XRPD results contained in the present invention is exemplary and should not be used for absolute comparison.

2. Thermal Analysis (1). Thermogravimetric Analysis

Appropriate amount of crystalline form A of mesaconine sample was placed on TA Q5000/Discovery 5500 thermogravimetric analyzer under the condition that protective gas was nitrogen, and the temperature was increased at a constant rate of 10° C./min in the range of room temperature to 350° C. to determine the change of mass with temperature so as to draw TGA curve (see FIG. 2). From the TGA curve, it can be seen that the crystalline form A sample had a weight loss of 2.1% when heated to 180° C.

(2). Differential Scanning Calorimetry

Appropriate amount of crystalline form A of mesaconine sample was placed on TA Q2000/Discovery 2500 differential scanning calorimeter under the condition that protective gas was nitrogen, and the temperature was increased at a constant rate of 10° C./min in the range of 25~250° C. to determine crystalline form A of mesaconine sample so as to draw DSC curve (see FIG. 3). DSC results showed that there was a sharp endothermic peak at 207.6° C. (initial temperature), which was the melting endothermic peak of crystalline form A of mesaconine.

(3). Melting Point

The crystalline form A of mesaconine was sampled and the melting point was determined according to "determination method of the melting point" (the first method of 0612, general rule, volume 4, the Chinese Pharmacopoeia, 2015 edition). The results were shown in table 2 below.

TABLE 2

| Batches | melting point (° C.) |
|---|---|
| crystalline form A of mesaconine sample | 206.6~208.4° C. |

The results showed that the melting phenomenon of the sample was obvious, and the melting point was in the range of 206~209° C.

Example 7

Stability, Solubility and Hygroscopicity of Crystalline Form A of Mesaconine

Crystalline form A of mesaconine prepared according to the method in Example 1 was sampled and subjected to the following tests.

A. Stability of Crystalline Form A of Msaconine

After the samples of crystalline form A of mesaconine were placed at 25° C., 60% RH and 40° C., 75% RH for 4 weeks, it was performed XRPD test. The test result was compared with XRPD spectrum of comparative sample of crystalline form A of the mesaconine (XRPD spectrum of crystalline form A of mesaconine before stability test), and the results were shown in FIG. 4. Another sample of crystalline form A of mesaconine was heated to 180° C., and then was performed XRPD test. The test result was compared with XRPD spectrum of comparative sample of crystalline form A of the mesaconine (XRPD spectrum of crystalline form A of mesaconine before stability test), and the results were shown in FIG. 5.

Figure 4:
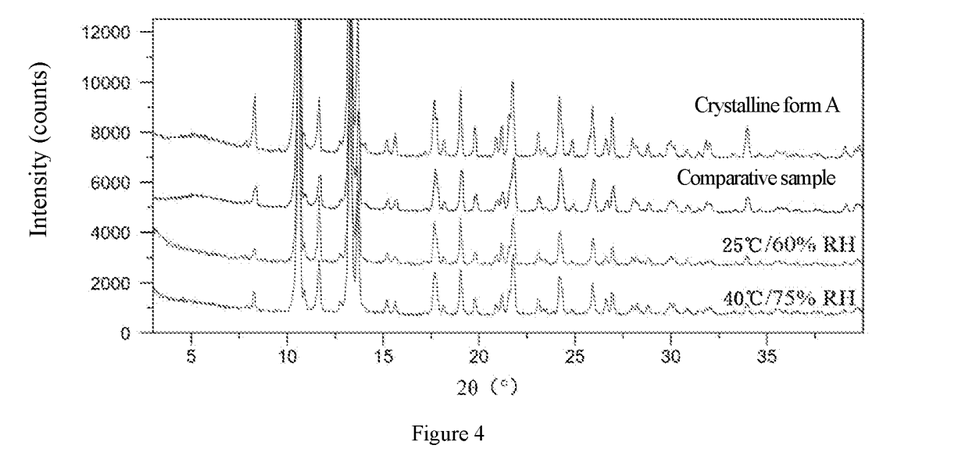
FIG. 4 is a comparison XRPD spectrum of the crystalline form A of mesaconine sample during stability test.
Figure 5:
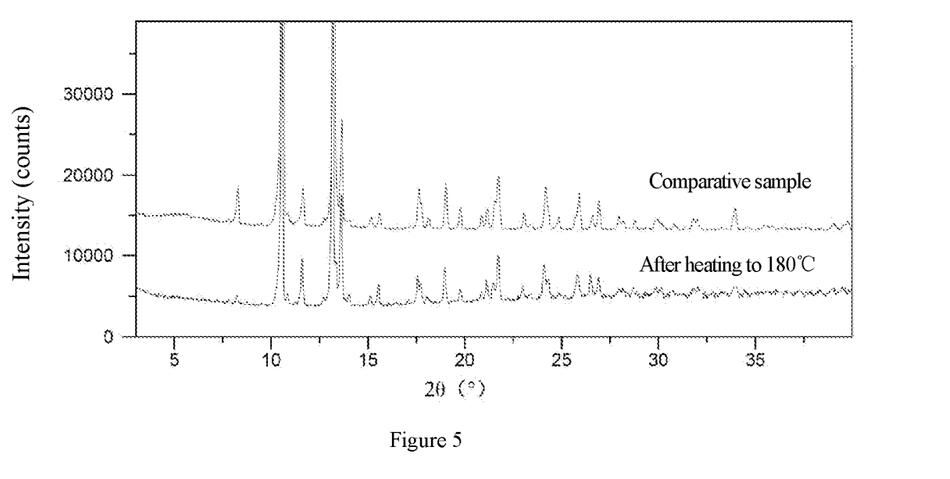
FIG. 5 is a comparison XRPD spectrum of the crystalline form A of mesaconine before and after heating to 180° C.

According to FIG. 4, after the samples of crystalline form A of mesaconine were placed at 25° C., 60% RH and 40° C., 75% RH for 4 weeks, the position and relative intensity of the main diffraction peaks in XRPD spectrum did not change significantly, which indicated that the crystalline form did not change, and they are still crystalline form A. According to FIG. 5, after the sample of crystalline form A of mesaconine was heated to 180° C., the position and relative intensity of the main diffraction peaks in XRPD spectrum did not changed significantly, which indicated that the crystalline form did not change, and it was still crystalline form A. The above test results showed that crystalline form A of mesaconine has good stability.

In addition, the crystalline form A of mesaconine was sampled and tested for influencing factors according to the Guiding principle for stability test of raw materials of drugs and preparations (general rule 9001, the Chinese pharmacopoeia, 2015 edition).

High temperature test: the sample was placed in an open flat weighing bottle at 60° C. for 10 days. Then the sample was tested according to the key inspection items of stability test, and analyzed by X-ray powder diffraction.

High humidity test: the sample was placed in an open flat weighing bottle at 25° C. and 90% relative humidity for 10 days. Then the sample was tested according to the key inspection items of stability test, and analyzed by X-ray powder diffraction.

Hard light irradiation test: the sample was placed in an open flat weighing bottle for 10 days under the illuminance of 4500 lx. Then the sample was tested according to the key inspection items of stability test, and analyzed by X-ray powder diffraction.

The results showed that the position and relative intensity of the main diffraction peaks in the X-ray powder diffraction spectrum had not changed significantly after the samples were subjected to the high temperature test, high humidity test and hard light irradiation test for 10 days.

The crystalline form A of mesaconine was further sampled and the melting point was determined according to the "determination method of melting point" (the first method of 0612, general rule, volume 4, the Chinese Pharmacopoeia, 2015 edition). As a result, the melting points of the samples were 207.0~208.9° C., 206.9~209.5° C. and 207.3~209.2° C. respectively after the samples were subjected to the above-mentioned high temperature test, high humidity test and hard light irradiation test for 10 days, which were basically consistent with the melting points (206.6~208.4° C.) of the samples before the test. The above test results showed that crystalline form A of mesaconine had good stability.

B. Solubility of Crystalline Form A of Mesaconine

The crystalline form A of mesaconine was sampled and tested according to the method of solubility test in the *Chinese pharmacopoeia* (2015 edition, general notice). The results were shown in table 3 below.

TABLE 3

| Solvent | Solubility | Description |
|---|---|---|
| Water | easily soluble | 1 g of solute can be dissolved in 1~10 ml of solvent |

The results in Table 3 showed that the crystalline form A of mesaconine was easily soluble in water, which indicated that crystalline form A of mesaconine had good solubility in water.

C. Hygroscopicity of Crystalline Form A of Mesaconine

The test was performed according to guiding principles for drug hygroscopicity test in *Chinese Pharmacopoeia*

(general rule 9103, volume 4, 2015 edition). Two batches of crystalline form A of mesaconine were sampled and tested, and the results were shown in Table 4:

TABLE 4

| No. | Percentage of weight increment(%) | Percentage of average weight increment(%) |
|---|---|---|
| Sample 1 | 0.85 | 0.85 |
| Sample 2 | 0.84 | |

According to the definition of hygroscopicity in *Chinese Pharmacopoeia* (general rule 9103, volume 4, 2015 edition): when the weight increment by hygroscopicity is less than 2% but not less than 0.2%, it has slight hygroscopicity. The weight increment of crystalline form A of mesaconine was 0.85% under the test conditions, which has slight hygroscopicity and good deliquescence resistance.

Example 8

Preparation of Crystalline Form B of Mesaconine 130 mg of crystalline form A of mesaconine sample was prepared according to the method in Example 1. The crystalline form A of mesaconine sample was suspended in 0.3 ml of N-methylpyrrolidone and stirred at 50° C. for 24 hours. Then the mixture was cooled to 20~30° C., stirred to precipitate crystal, and then filtrated. The obtained filter cake was vacuum dried at 85° C. for 10 hours to obtain white solid crystal. After testing, the white solid crystal was confirmed to be crystalline form B of mesaconine, and its XRPD spectrum was shown in FIG. 6. DSC spectrum showed (FIG. 8) that the crystalline form B of mesaconine of the present invention was a solvate of mesaconine and N-methylpyrrolidone.

Example 9

Preparation of Crystalline Form B of Mesaconine 400 mg of crystalline form A of mesaconine sample was prepared according to the method in Example 1. The crystalline form A of mesaconine sample was suspended in 0.9 ml of N-methylpyrrolidone and stirred at 40° C. for 36 hours. Then the mixture was cooled to 20~30° C., stirred to precipitate crystal, and then filtrated. The obtained filter cake was vacuum dried at 85° C. for 12 hours to obtain white solid crystal. After testing, the white solid crystal was confirmed to be crystalline form B of mesaconine, and its XRPD spectrum was consistent with that in FIG. 6.

Example 10

Characterization of Crystalline Form B of Mesaconine

The crystalline form B of mesaconine prepared according to the method in Example 8 was sampled and subjected to the following tests.
1. X-Ray Powder Diffraction Method
The crystalline form B of mesaconine was sampled and subjected to a test on PANalytical Empyrean and X'Pert3 X-ray powder diffraction analyzer under condition: Cu, Kα, Kα1 (Å): 1.540598; Kα2 (Å): 1.544426, Kα2/Kα1 intensity ratio: 0.50, scanning range: 3°~40°. The XRPD spectrum of the crystalline form B of mesaconine sample was shown in FIG. 6, and the basic information of the XRPD spectrum of the crystalline form B of mesaconine sample was shown in Table 5.

TABLE 5

| diffraction angle (2θ, °) | interplanar spacing (d, Å) | relative intensity (%) |
|---|---|---|
| 6.60 | 13.39 | 89.65 |
| 9.16 | 9.66 | 74.01 |
| 13.40 | 6.61 | 100.00 |
| 14.31 | 6.19 | 11.74 |
| 15.46 | 5.73 | 15.48 |
| 18.30 | 4.85 | 9.27 |
| 20.19 | 4.40 | 8.67 |
| 23.56 | 3.78 | 9.08 |
| 24.20 | 3.68 | 8.03 |

It should be understood by those skilled in the art that these diffraction peaks do not represent all the details of the diffraction peaks shown in the crystalline form B of mesaconine. The 2θ value of XRPD can change within the error range according to the testing equipments as well as the change during preparation and the change of batches, and the quoted value should not be regarded as absolute value. In addition, the relative intensity of the peaks may vary with the orientation effect, so the intensity shown in XRPD results contained in the present invention is exemplary and is not used for absolute comparison.

2. Thermal Analysis
(1). Thermogravimetric Analysis
Appropriate amount of crystalline form B of mesaconine sample was placed on TA Q5000/Discovery 5500 thermogravimetric analyzer under the condition that protective gas was nitrogen, and the temperature was increased at a constant rate of 10° C./min in the range of room temperature to 350° C. to determine the change of mass with temperature so as to draw TGA curve (see FIG. 7). From the TGA curve, it can be seen that the sample of crystalline form B had a weight loss of 3.0% when heated from room temperature to 115° C., and had a weight loss of 16.1% when heated to 185° C.

(2). Differential Scanning Calorimetry
Appropriate amount of crystalline form B of mesaconine sample was placed on TA Q2000/Discovery 2500 differential scanning calorimeter under the condition that protective gas was nitrogen, and the temperature was increased at a constant rate of 10° C./min in the range of 25~250° C. to determine crystalline form B of mesaconine sample so as to draw DSC curve (see FIG. 8). DSC results showed that there was a broad endothermic peak at 158.7° C. (peak temperature) and a sharp endothermic peak at 222.4° C. (initial temperature) which was the melting endothermic peak of crystalline form B of mesaconine.

Example 11

Stability of Crystalline Form B of Mesaconine

Crystalline form B of mesaconine prepared according to the method in Example 8 was sampled and subjected to the following tests.

Appropriate amount of crystalline form B of mesaconine was sampled and heated to 115° C., and then was performed XRPD test. The test result was compared with XRPD spectrum of comparative sample of crystalline form B of mesaconine (XRPD spectrum of crystalline form B of mesaconine before stability test), and the results were shown in FIG. 9.

Figure 9:
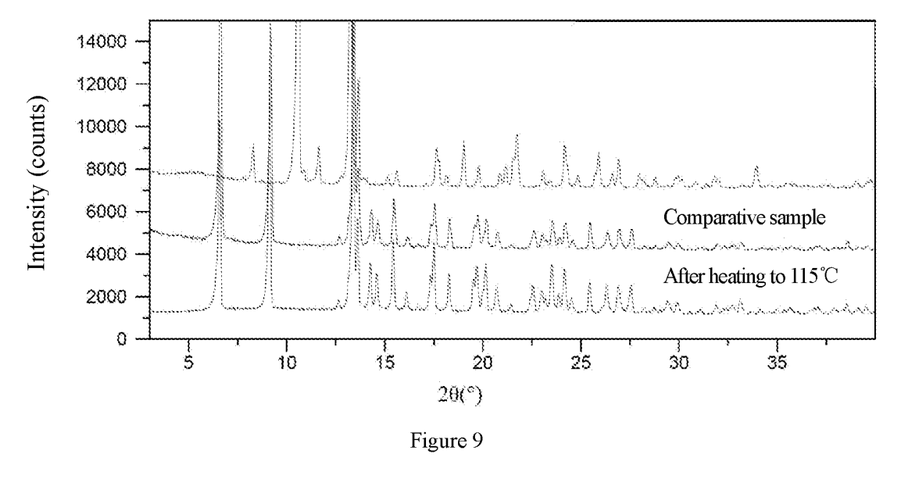
FIG. 9 is a comparison XRPD spectrum of the crystalline form B of mesaconine before and after heating to 115° C.

The results showed that the position and relative intensity of the main diffraction peaks of XRPD spectrum did not change obviously when the sample of crystalline form B of mesaconine was heated to 115° C., which indicated that the crystalline form did not change, and it was still crystalline form B. The above test results showed that crystalline form B of mesaconine has good stability.

Example 12

Preparation of Crystalline Form C of Mesaconine 100 mg of crystalline form B of mesaconine sample was prepared according to the method in Example 8. The crystalline form B of mesaconine sample was heated to 185° C. at vacuum for 24 hours to obtain white solid crystal. After testing, the white solid crystal was confirmed to be crystalline form C of mesaconine, and its XRPD spectrum was shown in FIG. 10.

Example 13

Preparation of Crystalline form C of Mesaconine 100 mg of crystalline form B of mesaconine sample was prepared according to the method in Example 8. The crystalline form B of mesaconine sample was heated to 190° C. at vacuum for 16 hours to obtain white solid crystal. After testing, the white solid crystal was confirmed to be crystalline form C of mesaconine, and its XRPD spectrum was consistent with that in FIG. 10.

Example 14

Characterization of Crystalline form C of Mesaconine

The crystalline form C of mesaconine prepared according to the method in Example 12 was sampled and subjected to the following tests.

1. X-Ray Powder Diffraction Method

The crystalline form C of mesaconine was sampled and subjected to a test on PANalytical Empyrean and X'Pert3 X-ray powder diffraction analyzer under condition: Cu, Kα, Kα1 (Å): 1.540598; Kα2 (Å): 1.544426, Kα2/Kα1 intensity ratio: 0.50, scanning range: 3°~40°. The X-ray diffraction spectrum of the crystalline form C of mesaconine sample was shown in FIG. 10, and the basic information of the XRPD spectrum of the crystalline form C of mesaconine sample was shown in Table 6.

TABLE 6

| XRPD Diffraction Peak List of crystalline form C Sample | | |
|---|---|---|
| diffraction angle (2θ, °) | interplanar spacing (d, Å) | relative intensity (%) |
| 7.90 | 11.20 | 97.03 |
| 10.12 | 8.74 | 16.58 |
| 13.03 | 6.80 | 100.00 |
| 17.35 | 5.11 | 20.15 |
| 19.44 | 4.57 | 10.39 |
| 19.86 | 4.47 | 6.69 |
| 21.03 | 4.23 | 8.45 |

TABLE 6-continued

| XRPD Diffraction Peak List of crystalline form C Sample | | |
|---|---|---|
| diffraction angle (2θ, °) | interplanar spacing (d, Å) | relative intensity (%) |
| 23.78 | 3.74 | 17.82 |
| 26.60 | 3.35 | 7.29 |

It should be understood by those skilled in the art that these diffraction peaks do not represent all the details of the diffraction peaks shown in the crystalline form C of mesaconine. The 2θ value of XRPD can change within the error range according to the testing equipments as well as the change during preparation and the change of batches, and the quoted value should not be regarded as absolute value. In addition, the relative intensity of the peaks may vary with the orientation effect, so the intensity shown in XRPD results contained in the present invention is exemplary and is not used for absolute comparison.

2. Thermal Analysis (1). Thermogravimetric Analysis

Appropriate amount of crystalline form C of mesaconine sample was placed on TA Q5000/Discovery 5500 thermogravimetric analyzer under the condition that protective gas was nitrogen, and the temperature was increased at a constant rate of 10° C./min in the range of room temperature to 350° C. to determine the change of mass with temperature so as to draw TGA curve (see FIG. 11). From the TGA curve, it can be seen that the crystalline form C had a weight loss of 0.5% when heated from room temperature to 185° C.

(2). Differential Scanning Calorimetry

Appropriate amount of crystalline form C of mesaconine sample was placed on TA Q2000/Discovery 2500 differential scanning calorimeter under the condition that protective gas was nitrogen, and the temperature was increased at a constant rate of 10° C./min in the range of 25~250° C. to determine crystalline form C of mesaconine sample so as to draw DSC curve (see FIG. 12). DSC results showed that there was a sharp endothermic peak at 224.4° C. (initial temperature), which was the melting endothermic peak of crystalline form C of mesaconine.

The invention claimed is:

1. Crystalline form A of mesaconine, wherein, the crystalline form A of mesaconine exhibits characteristic peaks at 2θ of 8.3°±0.2°, 10.6°±0.2°, 13.3°±0.2°, 13.7°±0.2° and 19.0°±0.2° in powder X-ray diffraction spectrum using Cu-Kα radiation.

2. The crystalline form A of mesaconine according to claim 1, wherein, the crystalline form A of mesaconine also exhibits characteristic peaks at 2θ of 11.6°±0.2°, 19.8°±0.2°, 24.2°±0.2° and 26.9°±0.2° in powder X-ray diffraction spectrum using Cu-Kα radiation.

3. A method for preparing the crystalline form A of mesaconine according to claim 1, wherein, the method comprises steps of:

(1) adding mesaconine into a solvent, then heating the obtained solution to 50~90° C. to dissolve the mesaconine so as to obtain a mesaconine solution;

(2) cooling the mesaconine solution to −10~30° C., stirring the solution to precipitate crystal, and then performing filtration;

(3) drying the solid obtained by filtration in the step (2) at vacuum to obtain the crystalline form A of mesaconine.

4. The method according to claim 3, wherein, the solvent is selected from a group consisting of water, methanol, ethanol, isopropanol, acetone and acetonitrile and combinations thereof.

5. A pharmaceutical composition comprising the crystalline form A of mesaconine according to claim 1, and pharmaceutically acceptable excipients.

6. A method for treating heart failure in a subject, comprising administering thereto an effective amount of a crystalline form A of mesaconine according to claim 1, or a pharmaceutical composition comprising the crystalline form A of mesaconine and pharmaceutically acceptable excipients.

* * * * *